US00PP15881P2

(12) United States Plant Patent
Westhoff

(10) Patent No.: US PP15,881 P2
(45) Date of Patent: Jul. 19, 2005

(54) *SANVITALIA* PLANT NAMED 'WESSACOMP'

(50) Latin Name: *Sanvitalia speciosa*
Varietal Denomination: Wessacomp

(75) Inventor: Heinrich Westhoff, Südlohn (DE)

(73) Assignee: Josef und Heinrich Westhoff Gartenbau-Spezialkulturen, Südlohn (DE)

( * ) Notice: Subject to any disclaimer, the term of this patent is extended or adjusted under 35 U.S.C. 154(b) by 2 days.

(21) Appl. No.: 10/920,829

(22) Filed: Aug. 18, 2004

(51) Int. Cl.[7] ..... A01H 5/00

(52) U.S. Cl. ..... Plt./263

(58) Field of Search ..... Plt./263

(56) References Cited

U.S. PATENT DOCUMENTS

PP14,799 P3 * 5/2004 Westhoff ..... Plt./263
PP14,924 P2 * 6/2004 Houbraken ..... Plt./263

OTHER PUBLICATIONS

UPOV ROM GTITM Computer Database, GTI Jouve Retrieval Software 2004/04 Citations for 'Wessacomp'.*

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct cultivar of *Sanvitalia* plant named 'Wessacomp', characterized by its compact and mostly upright, low mounding plant habit; small dark green-colored leaves; freely branching habit and short internodes; dense and bushy plant form; freely flowering habit; and bright yellow-colored ray florets.

1 Drawing Sheet

Botanical designation: *Sanvitalia speciosa.*
Variety denomination: 'Wessacomp'.

BACKGROUND OF THE INVENTION

The present Invention relates to a new and distinct cultivar of *Sanvitalia* plant, botanically known as *Sanvitalia speciosa* and hereinafter referred to by the name 'Wessacomp'.

The new *Sanvitalia* was discovered by the Inventor in 2002 as a naturally-occurring whole plant mutation of the *Sanvitalia speciosa* cultivar Aztekengold, not patented, in a controlled environment in Südlohn, Germany. Specifically, the claimed plant originated as a cutting from the cultivar 'Aztekengold' that exhibited desirable, mutated characteristics. The new *Sanvitalia* was selected by the Inventor on the basis of its compact plant habit.

Asexual reproduction of the new *Sanvitalia* by vegetative cuttings was first conducted in Südlohn, Germany in 2002. Asexual reproduction by vegetative cuttings has shown that the unique features of this new *Sanvitalia* are stable and reproduced true to type in successive generations.

SUMMARY OF THE INVENTION

The cultivar Wessacomp has not been observed under all possible environmental conditions. The phenotype may vary somewhat with variations in environment such as temperature and light level without, however, any variance in genotype.

The following traits have been repeatedly observed and are determined to be the unique characteristics of 'Wessacomp'. These characteristics in combination distinguish 'Wessacomp' as a new and distinct *Sanvitalia:*

1. Compact and mostly upright, low mounding plant habit.

2. Small dark green-colored leaves.
3. Freely branching habit and short internodes; dense and bushy plant form.
4. Freely flowering habit.
5. Bright yellow-colored ray florets.

Compared to plants of the parent, the cultivar Aztekengold, plants of the new *Sanvitalia* are more compact, more upright and have shorter internodes.

Plants of the new *Sanvitalia* can be compared to plants of the *Sanvitalia* cultivar Santanis, disclosed in U.S. Plant Pat. No. 14,924. In side-by-side comparisons conducted in Südlohn, The Netherlands, plants of the new *Sanvitalia* differed from plants of the cultivar Santanis in the following characteristics:

1. Plants of the new *Sanvitalia* were more compact than plants of the cultivar Santanis.
2. Plants of the new *Sanvitalia* had shorter internodes than plants of the cultivar Santanis.
3. Plants of the new *Sanvitalia* had smaller leaves than plants of the cultivar Santanis.

Plants of the new *Sanvitalia* can also be compared to plants of the *Sanvitalia* cultivar Wessastar, disclosed in U.S. Plant Pat. No. 14,799. In side-by-side comparisons conducted in Südlohn, The Netherlands, plants of the new *Sanvitalia* differed from plants of the cultivar Wessastar in the following characteristics:

1. Plants of the new *Sanvitalia* were more compact than plants of the cultivar Wessastar.
2. Plants of the new *Sanvitalia* had shorter internodes than plants of the cultivar Wessastar.
3. Plants of the new *Sanvitalia* had smaller leaves than plants of the cultivar Wessastar.
4. Plants of the new *Sanvitalia* had smaller sepals than plants of the cultivar Wessastar.

BRIEF DESCRIPTION OF THE PHOTOGRAPHS

The accompanying colored photographs illustrate the overall appearance of the new *Sanvitalia* showing the colors as true as it is reasonably possible to obtain in colored reproductions of this type. Colors in the photographs may differ from the color values cited in the detailed botanical description which accurately describe the colors of the new *Sanvitalia*.

The photograph at the top of the sheet comprises a side perspective view of a typical flowering plant of 'Wessacomp' grown in a container.

The photograph at the bottom of the sheet comprises a close-up view of a typical inflorescence of 'Wessacomp'.

DETAILED BOTANICAL DESCRIPTION

The aforementioned photographs and following observations and measurements describe plants grown in Südlohn, Germany, under commercial practice during the spring and summer in a glass-covered greenhouse with day temperatures ranging from 20 to 25° C. and night temperatures ranging from 16 to 18° C. Plants used for the photographs and botanical description were grown in 10-cm containers for about 20 weeks.

In the following description, color references are made to The Royal Horticultural Society Colour Chart, 1995 Edition, except where general terms of ordinary dictionary significance are used.

Botanical classification: *Sanvitalia speciosa* cultivar Wessacomp.

Parentage: Naturally-occurring whole plant mutation of the *Sanvitalia speciosa* cultivar Aztekengold, not patented.

Propagation:

*Type.*—Vegetative cuttings.

*Time to initiate roots.*—Summer: About 16 days at 18° C. Winter: About 18 days at 18° C.

*Time to produce a rooted young plant.*—Summer: About 26 days at 18° C. Winter: About 28 days at 18° C.

*Root description.*—Fine; vigorous, freely branching; white in color.

Plant description:

*Appearance.*—Compact and mostly upright; low mounding plant habit. Freely branching with two lateral branches developing at every node; indeterminate growth habit; moderately vigorous.

*Plant height.*—About 7 to 10 cm.

*Plant width.*—About 9 to 10 cm.

*Lateral branches.*—Length: About 5.3 cm. Diameter: About 1.3 mm. Internode length: About 8.3 mm. Strength: Moderately strong. Texture: Densely pubescent. Color: 146D overlain with a mixture 166A, 187A and 187B.

*Foliage description.*—Arrangement: Opposite, simple; decussate; sessile. Length: About 2.1 cm. Width: About 8 mm. Shape: Lanceolate to elliptic. Apex: Acute. Base: Cordate. Margin: Entire. Texture, upper and lower surfaces: Pubescent. Venation pattern: Pinnate. Color: Developing foliage, upper surface: 137A. Developing foliage, lower surface: 138B. Mature foliage, upper surface: 147A overlain with a mixture of 166A, 187A and 187B. Mature foliage, lower surface: 147C. Venation, upper surface: 145C overlain with 166A. Venation, lower surface: 145C.

Inflorescence description:

*Appearance.*—Daisy-type inflorescence form with elongated oblong-shaped ray florets. Solitary inflorescences borne on terminals above foliage. Disc and ray florets develop acropetally on a capitulum. Inflorescences persistent. Inflorescences not fragrant.

*Quantity.*—Freely flowering; one terminal inflorescence per lateral branch.

*Flowering response.*—Early flowering, plants begin to flower about four weeks after planting unrooted cuttings. Plants flower continuously from April until frost in the Autumn in the garden.

*Inflorescence longevity.*—Inflorescences maintain good color and substance for about three to four weeks on the plant.

*Inflorescence bud.*—Height: About 2.9 mm. Diameter: About 4.1 mm. Shape: Oblate. Color: 146A occasionally overlain with 187A.

*Inflorescence size.*—Diameter: About 1.6 cm. Depth (height): About 5 mm. Diameter of disc: About 6 mm.

*Ray florets.*—Quantity/arrangement: About 13 ray florets per inflorescence arranged in a single whorl. Orientation: Initially upright, then about 90° from vertical and reflexing with subsequent development. Length: About 5.5 mm. Width: About 2.3 mm. Shape: Elongated oblong. Apex: Rounded to obtuse. Base: Attenuate. Margin: Entire. Texture, upper and lower surfaces: Smooth, glabrous; satiny. Color: When opening and fully opened, upper surface: 12A to 17A. When opening and fully opened, lower surface: 144B to 151A.

*Disc florets.*—Quantity/arrangement: About 120 disc florets per inflorescence massed at center of receptacle. Length: About 1.5 mm. Width: At apex, about 1 mm; at base, less than 1 mm. Shape: Tubular; minute. Apex: Five-pointed. Color, immature: 144A. Color, mature: 153A.

*Phyllaries.*—Quantity/arrangement: About five to seven in a single whorl. Length: About 4.8 mm. Width: About 3.1 mm. Shape: Rounded. Apex: Acute. Base: Fused. Margin: Entire. Texture, upper and lower surfaces: Smooth, glabrous. Color, upper and lower surfaces: 146A to 146B.

*Peduncles.*—Length: About 9 mm. Diameter: About 1 mm. Strength: Moderately strong; wiry. Texture: Smooth, glabrous. Color: 145B overlain with a mixture of 166A, 187A and 187B.

*Reproductive organs.*—Androecium: Present on disc florets only. Stamen quantity: Five per floret. Anther length: About 1.2 mm. Anther diameter: About 0.3 mm. Anther shape: Oblong. Anther color: 17A. Filament length: About 2.4 mm. Filament color: 155D. Pollen amount: Moderate to scarce. Pollen color: 17A. Gynoecium: Present on both ray and disc florets. Pistil quantity: One per floret. Pistil length: About 2.8 mm. Stigma shape: Bi-parted. Stigma color: 17B. Style length: About 1.4 mm. Style color: 17D. Ovary color: 146D to 145A.

*Seed.*—Length: About 2.1 mm. Diameter: About 1.3 mm. Shape: Ovate to reniform. Color: 195A.

Disease/pest resistance: Resistance to pathogens and pests common to *Sanvitalias* has not been observed on plants grown under commercial greenhouse conditions.

Weather tolerance: Plants of the new *Sanvitalia* have been observed to have good garden performance and have been observed to be tolerant to rain, wind and temperatures from 2 to 30° C.

It is claimed:

1. A new and distinct cultivar of *Sanvitalia* plant named 'Wessacomp', as illustrated and described.

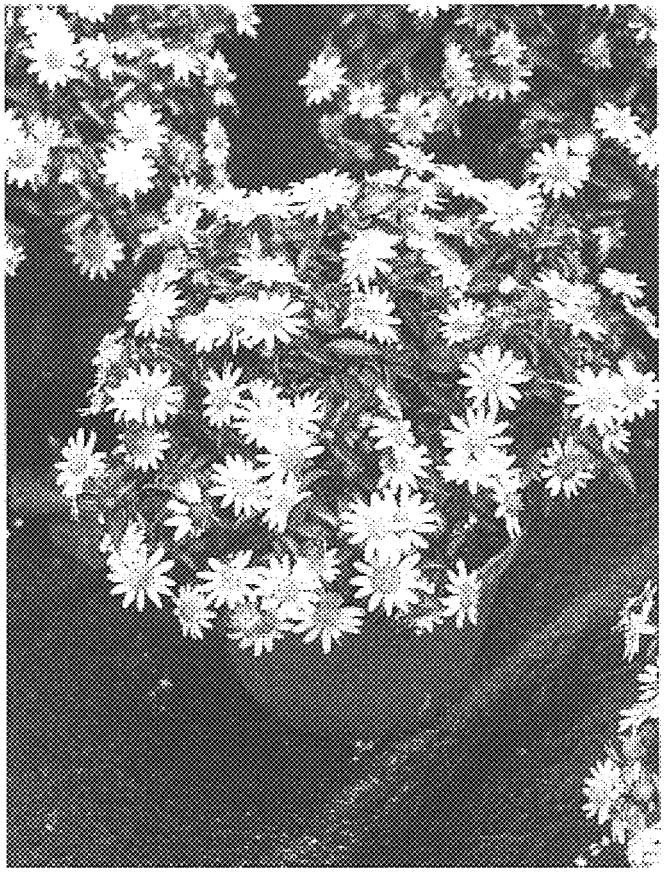
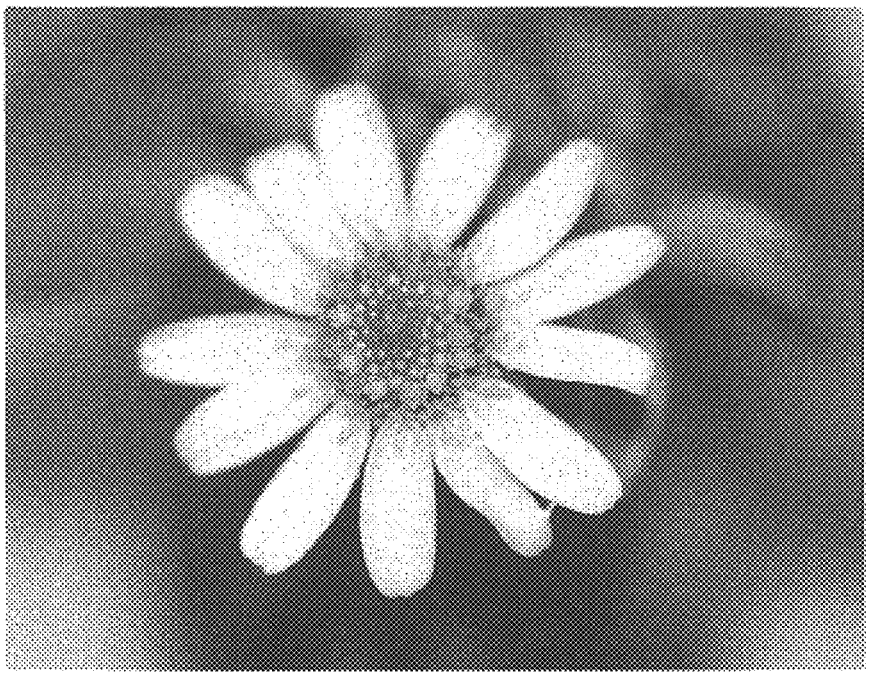

* * * * *